US011026838B2

(12) United States Patent
Raksi

(10) Patent No.: US 11,026,838 B2
(45) Date of Patent: *Jun. 8, 2021

(54) PHOTODISRUPTIVE LASER FRAGMENTATION OF TISSUE

(71) Applicant: Alcon LenSx, Inc., Aliso Viejo, CA (US)

(72) Inventor: Ferenc Raksi, Mission Viejo, CA (US)

(73) Assignee: Alcon Inc.

( * ) Notice: Subject to any disclaimer, the term of this patent is extended or adjusted under 35 U.S.C. 154(b) by 748 days.

This patent is subject to a terminal disclaimer.

(21) Appl. No.: 15/222,730

(22) Filed: Jul. 28, 2016

(65) Prior Publication Data

US 2016/0331590 A1 Nov. 17, 2016

Related U.S. Application Data

(63) Continuation of application No. 14/451,881, filed on Aug. 5, 2014, now Pat. No. 9,427,356, which is a continuation of application No. 12/351,784, filed on Jan. 9, 2009, now abandoned.

(60) Provisional application No. 61/020,115, filed on Jan. 9, 2008.

(51) Int. Cl.
*A61F 9/008* (2006.01)
*A61F 9/007* (2006.01)

(52) U.S. Cl.
CPC .......... *A61F 9/00825* (2013.01); *A61F 9/008* (2013.01); *A61F 9/00736* (2013.01); *A61B 2217/005* (2013.01); *A61F 2009/0087* (2013.01); *A61F 2009/00844* (2013.01); *A61F 2009/00897* (2013.01)

(58) Field of Classification Search
CPC .............................. A61F 9/008; A61B 18/20
See application file for complete search history.

(56) References Cited

U.S. PATENT DOCUMENTS

| 4,081,207 | A | * | 3/1978 | Dippel | ..................... G02B 5/04 348/E3.01 |
| 4,481,948 | A | | 11/1984 | Sole | |
| 4,538,608 | A | | 9/1985 | L'Esperance, Jr. | |
| 4,554,917 | A | | 11/1985 | Tagnon | |

(Continued)

FOREIGN PATENT DOCUMENTS

| EP | 1252872 | 10/2002 |
| KR | 2002-0093935 | 12/2002 |

(Continued)

OTHER PUBLICATIONS

European Supplementary Search Report for European Application No. 08843434, dated Dec. 16, 2010.

(Continued)

*Primary Examiner* — Lynsey C Eiseman

(57) ABSTRACT

An ophthalmic laser surgical system includes a pulsed laser source configured to generate a pulsed laser beam, optics configured to direct the laser beam towards a target region in a lens of an eye, and a processor configured to control the optics to form a regular array of cells in the target region by creating layers of photodisrupted bubbles to generate cell boundaries. The layers are created by causing the optics to scan the pulsed laser according to a curvature of a focal plane of the optics to track a natural curvature of the lens.

8 Claims, 9 Drawing Sheets

(56) References Cited

U.S. PATENT DOCUMENTS

| | | |
|---|---|---|
| 4,633,866 A | 1/1987 | Peyman et al. |
| 4,638,801 A | 1/1987 | Daly et al. |
| 4,686,366 A | 8/1987 | Stuke |
| 4,694,828 A | 9/1987 | Eichenbaum |
| 4,766,896 A | 8/1988 | Pao |
| 4,888,015 A | 12/1989 | Domino |
| 4,907,586 A | 3/1990 | Bille et al. |
| 5,013,319 A | 5/1991 | Davis |
| 5,036,592 A | 8/1991 | Marshall |
| 5,089,022 A | 2/1992 | Koester et al. |
| 5,139,022 A | 8/1992 | Lempert |
| 5,225,862 A | 7/1993 | Nagano et al. |
| 5,246,435 A | 9/1993 | Bille et al. |
| 5,261,923 A | 11/1993 | Soares |
| 5,269,787 A | 12/1993 | Cozean, Jr. et al. |
| 5,333,018 A | 7/1994 | Heine et al. |
| 5,336,215 A | 8/1994 | Hsueh et al. |
| 5,423,841 A | 6/1995 | Kornefeld |
| 5,439,462 A | 8/1995 | Bille et al. |
| 5,442,412 A | 8/1995 | Frey et al. |
| 5,520,679 A | 5/1996 | Lin |
| 5,549,632 A | 8/1996 | Lai |
| 5,656,186 A | 8/1997 | Mourou et al. |
| 5,669,923 A | 9/1997 | Gordon |
| 5,738,677 A | 4/1998 | Colvard et al. |
| 5,957,921 A | 9/1999 | Mirhashemi et al. |
| 5,968,095 A | 10/1999 | Norrby |
| 5,984,916 A | 11/1999 | Lai |
| 5,987,151 A | 11/1999 | Akashi |
| 5,993,438 A | 11/1999 | Juhasz et al. |
| 6,004,314 A | 12/1999 | Wei et al. |
| 6,010,497 A | 1/2000 | Tang et al. |
| 6,066,138 A | 5/2000 | Sheffer et al. |
| 6,099,522 A | 8/2000 | Knopp et al. |
| 6,146,375 A | 11/2000 | Juhasz et al. |
| 6,165,190 A | 12/2000 | Nguyen |
| 6,197,018 B1 | 3/2001 | O'Donnell, Jr. |
| 6,217,570 B1 | 4/2001 | Nevyas |
| 6,254,595 B1 | 7/2001 | Juhasz et al. |
| 6,322,556 B1 | 11/2001 | Gwon et al. |
| 6,328,732 B1 | 12/2001 | Donitzky et al. |
| 6,344,040 B1 | 2/2002 | Juhasz et al. |
| RE37,585 E | 3/2002 | Mourou et al. |
| 6,379,005 B1 | 4/2002 | Williams et al. |
| 6,391,020 B1 | 5/2002 | Kurtz et al. |
| 6,409,718 B1 | 6/2002 | Tang |
| 6,451,006 B1 | 9/2002 | Bille |
| 6,454,761 B1 | 9/2002 | Freedman |
| 6,508,812 B1 | 1/2003 | Williams et al. |
| 6,579,282 B2 | 6/2003 | Bille et al. |
| 6,610,051 B2 | 8/2003 | Bille |
| 6,620,160 B2 | 9/2003 | Lewis et al. |
| 6,623,476 B2 | 9/2003 | Juhasz et al. |
| 6,676,653 B2 | 1/2004 | Juhasz et al. |
| 6,712,809 B2 | 3/2004 | Li et al. |
| 6,726,679 B1 | 4/2004 | Dick et al. |
| 6,730,074 B2 | 5/2004 | Bille et al. |
| 6,751,033 B2 | 6/2004 | Goldstein et al. |
| 6,863,667 B2 | 3/2005 | Webb et al. |
| 6,899,707 B2 | 5/2005 | Scholler et al. |
| 6,902,561 B2 | 6/2005 | Kurtz et al. |
| 6,913,603 B2 | 7/2005 | Knopp et al. |
| 6,986,763 B2 | 1/2006 | Holmén |
| 6,991,629 B1 | 1/2006 | Juhasz et al. |
| 7,018,376 B2 | 3/2006 | Webb et al. |
| 7,027,233 B2 | 4/2006 | Goldstein et al. |
| 7,044,602 B2 | 5/2006 | Chernyak |
| 7,101,364 B2 | 9/2006 | Bille |
| 7,131,968 B2 | 11/2006 | Bendett et al. |
| 7,284,858 B2 | 10/2007 | Bergner et al. |
| 7,371,230 B2 | 5/2008 | Webb et al. |
| 7,390,089 B2 | 6/2008 | Loesel et al. |
| 7,391,520 B2 | 6/2008 | Zhou et al. |
| 7,402,159 B2 | 7/2008 | Loesel et al. |
| 7,742,173 B2 | 6/2010 | Yun et al. |
| 2002/0013574 A1 | 1/2002 | Elbrecht et al. |
| 2002/0097374 A1 | 7/2002 | Payne et al. |
| 2002/0133145 A1 | 9/2002 | Gerlach et al. |
| 2002/0193704 A1 | 12/2002 | Goldstein et al. |
| 2003/0073983 A1 | 4/2003 | Bille |
| 2004/0044355 A1 | 3/2004 | Nevyas |
| 2004/0102765 A1 | 5/2004 | Koenig |
| 2004/0106929 A1 | 6/2004 | Masket |
| 2004/0151466 A1 | 8/2004 | Crossman-Bosworth et al. |
| 2004/0199149 A1 | 10/2004 | Myers et al. |
| 2004/0243111 A1 | 12/2004 | Bendett et al. |
| 2004/0243112 A1 | 12/2004 | Bendett et al. |
| 2004/0243113 A1 | 12/2004 | Sugiura et al. |
| 2004/0243233 A1 | 12/2004 | Phillips |
| 2004/0254568 A1 | 12/2004 | Rathjen |
| 2005/0015120 A1 | 1/2005 | Seibel et al. |
| 2005/0081393 A1 | 4/2005 | Su et al. |
| 2005/0090813 A1 | 4/2005 | Schweitzer et al. |
| 2005/0107773 A1 | 5/2005 | Bergt et al. |
| 2005/0165387 A1 | 7/2005 | Lubatschowski et al. |
| 2005/0173817 A1 | 8/2005 | Fauver et al. |
| 2005/0245915 A1 | 11/2005 | Loesel et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0192921 A1 | 8/2006 | Loesel et al. |
| 2006/0195076 A1 | 8/2006 | Blumenkranz et al. |
| 2006/0217688 A1 | 9/2006 | Lai |
| 2006/0235428 A1 | 10/2006 | Silvestrini |
| 2006/0264990 A1 | 11/2006 | Michelson et al. |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173759 A1 | 7/2007 | Augustine et al. |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0189664 A1 | 8/2007 | Andersen et al. |
| 2007/0230520 A1 | 10/2007 | Mordaunt et al. |
| 2008/0033406 A1 | 2/2008 | Andersen et al. |
| 2008/0049188 A1 | 2/2008 | Wiltberger et al. |
| 2008/0071254 A1 | 3/2008 | Lummis et al. |
| 2008/0088795 A1 | 4/2008 | Goldstein et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0048586 A1 | 2/2009 | Krueger et al. |
| 2009/0088734 A1 | 4/2009 | Mordaunt |
| 2009/0137988 A1 | 5/2009 | Kurtz |
| 2009/0137991 A1 | 5/2009 | Kurtz |
| 2009/0137993 A1 | 5/2009 | Kurtz |
| 2009/0143772 A1 | 6/2009 | Kurtz |
| 2009/0149840 A1 | 6/2009 | Kurtz |
| 2009/0149841 A1 | 6/2009 | Kurtz |
| 2009/0171327 A1* | 7/2009 | Kurtz ............... A61F 9/008 606/6 |
| 2010/0004641 A1 | 1/2010 | Frey et al. |
| 2010/0004643 A1 | 1/2010 | Frey et al. |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |

(56) References Cited

U.S. PATENT DOCUMENTS

2010/0324542 A1    12/2010    Kurtz et al.
2010/0324543 A1    12/2010    Kurtz et al.

FOREIGN PATENT DOCUMENTS

WO        98/27863      7/1998
WO        03/022168     3/2003
WO        2007-0103349   9/2007

OTHER PUBLICATIONS

International Search Report and Written Opinion dated Feb. 17, 2012 for International Application No. PCT/US2011/041677.
International Search Report and Written Opinion dated Feb. 17, 2012 for International Application No. PCT/US2011/041700.
Toyran S. et al., 2005, "Femtosecond laser photodisruption of human trabecular meshwork: an in vitro study", Experimental Eye Research, vol. 81, 298-305.
European Patent Office, European Application No. 09700876.7, filed Jan. 9, 2009, in Search Report dated Aug. 10, 2011, 3 pages.
Chinn, S.R., et al., "Optical coherence tomography using a frequency-tunable optical source," *Optics Letters,* 22(5):340-342, Mar. 1997.
Freel, C., et al., "Analysis of nuclear fiber cell compaction in transparent and cataractous diabetic human lenses by scanning electron microscopy," *BMC Ophthalmology,* 3(1):1-9, Jan. 2003.
Heys, K.R., et al., "Massive increase in the stiffness of the human lens nucleus with age: the basis for presbyopia?" *Molecular Vision,* 10:956-963, Dec. 2004.
Huber, R., et al., "Three-dimensional and C-mode OCT imaging with a compact, frequency swept laser source at 1300 nm," *Optics Express,* 13(26):10523-10538, Dec. 2005.
International Search Report and Written Opinion dated Sep. 13, 2010 for International Application No. PCT/US2009/069510, filed Sep. 18, 2008 (13 pages).
Sweeney, M.H.J., et al., "An Impediment to Glutathione Diffusion in Older Normal Human Lenses: a Possible Precondition for Nuclear Cataract," *Experimental Eye Research,* 67(5):587-595, Nov. 1998.
Yun, S.H., et al., "Wavelength-Swept Fiber Laser with Frequency Shifted Feedback and Resonantly Swept Intra-Cavity Acoustooptic Tunable Filter," IEEE Journal of Selected Topics in Quantum Electronics, 3(4):1087-1096, Aug. 1997.
Hammer, D., et al., "Shielding properties of laser-induced breakdown in water for pulse durations from 5 ns to 125 fs," *Applied Optics,* 36(22):5630-5640, Aug. 1997.
International Search Report and Written Opinion dated Jun. 30, 2009 for International Application No. PCT/US2008/082156, filed Oct. 31, 2008 (9 pages).
International Search Report and Written Opinion dated Mar. 12, 2009 for International Application No. PCT/US2008/075506, filed Sep. 5, 2008 (10 pages).
International Search Report and Written Opinion dated Mar. 17, 2009 for International Application No. PCT/US2008/075509, filed Sep. 5, 2008 (10 pages).
International Search Report and Written Opinion dated Mar. 18, 2009 for International Application No. PCT/US2008/076890, filed Sep. 18, 2008 (8 pages).
International Search Report and Written Opinion dated Mar. 27, 2009 for International Application No. PCT/US2008/075911, filed Sep. 10, 2008 (9 pages).
International Search Report and Written Opinion dated Mar. 30, 2009 for International Application No. PCT/US2008/076910, filed Sep. 18, 2008 (9 pages).
Vogel, A., et al., "Intraocular Photodisruption with Picosecond and Nanosecond Laser Pulses: Tissue Effects in Cornea, Lens, and Retina," *Ophthalmology & Visual Science,* 35(7):3032-3044, Jun. 1994.
International Search Report and Written Opinion dated Jul. 31, 2009 for International Application No. PCT/US2009/030676, filed Jan. 9, 2009 (9 pages).

* cited by examiner

Spots Hit by Laser

Eye Lens
Cornea
Eye
Aspiration Device for Removing Lens Material

PHOTODISRUPTIVE LASER FRAGMENTATION OF TISSUE

This application is a continuation of, and thus claims benefit of and priority from, U.S. patent application "Photodisruptive Laser Fragmentation of Tissue," Ser. No. 14/451,881, filed Aug. 5, 2014 which is a continuation of U.S. patent application "Photodisruptive laser fragmentation of tissue," Ser. No. 12/351,784, filed Jan. 9, 2009, that claims benefit of and priority from U.S. provisional application "Photodisruptive laser fragmentation of tissue", Ser. No. 61/020,115, filed Jan. 9, 2008, the disclosures of which are hereby incorporated by reference in their entirety.

BACKGROUND

This application relates to laser surgery techniques and systems for operating on eyes.

Laser light can be used to perform surgical operations on various parts of an eye for vision correction and other medical treatment. Techniques for performing such procedures with higher efficiency may provide desired benefits.

SUMMARY

A method of photodisruptive laser surgery and corresponding system are provided. In some implementations the method of fragmenting biological tissue with a photodisruptive laser includes selecting a target region of the tissue for fragmentation, directing a beam of laser pulses to the selected target region of the tissue, and forming cells in the target region of the tissue by directing the laser beam to generate cell boundaries.

In some implementations the tissue is a tissue of an eye.

In some implementations the tissue is a crystalline lens of the eye.

In some implementations the method further includes inserting an aspiration needle into the target region and removing fragmented tissue from the target region already scanned by the laser beam by using the aspiration needle.

In some implementations the forming the cells includes forming cells with size sufficiently small to pass through the aspiration needle.

In some implementations the forming the cells includes forming the cells arranged in an array.

In some implementations the array is a regular array.

In some implementations the regular array is one of a simple cubic lattice, a face centered lattice, a body centered lattice, a hexagonal lattice, a Bravais lattice, and a stack of two dimensional lattices.

In some implementations the array is essentially a random array.

In some implementations the forming the cells includes fragmenting the target tissue into cells of spheres or polyhedra.

In some implementations the forming the cells includes scanning the laser beam to form multiple cells in parallel in a layer.

In some implementations the forming the cells includes directing the laser beam to form individual cells successively.

In some implementations the forming the cells includes scanning the laser beam to form a cell array progressing from a posterior to an anterior direction, or scanning the laser beam to form a cell array progressing from an anterior to a posterior direction.

In some implementations the directing the laser beam to generate cell boundaries includes generating the cell boundaries by creating layers of bubbles in the target region of the tissue.

In some implementations the creating layers of bubbles includes creating a layer of bubbles by applying a laser beam with an essentially constant power, or with a varying power.

In some implementations the directing the beam of laser pulses includes applying the laser pulses with a laser parameter of at least one of: a pulse duration between 0.01 picosecond and 50 picoseconds, a repetition rate between 10 kiloHertz and 100 megaHertz, a pulse energy between 1 microJoule and 25 microJoule, and a pulse target separation between 0.1 micron and 50 microns.

In some implementations the directing the beam of laser pulses comprises applying the laser pulses with a laser parameter based on a preoperative measurement of structural properties of the target region of the tissue, or an age dependent algorithm.

In some implementations the method also includes applying additional laser pulses to one or more locations outside the target region of the tissue to create an opening for an additional procedure.

In some implementations the method includes identifying a surgical goal, and selecting laser parameters and method features to achieve the identified surgical goal.

In some implementations the surgical goal is an optimization of one or more of a speed of the method of fragmenting, a total amount of energy applied to the eye during the fragmenting, and a total number of generated bubbles.

In some implementation the surgical goal is one or more of: maximization of the speed of the method of fragmenting, minimization of the total amount of energy applied to the eye during the fragmenting, and minimization of the total number of generated bubbles.

In some implementations the method includes selecting laser parameters and method features to achieve a total time of fragmentation of one of less than 2 minutes, less than 1 minute, and less than 30 seconds.

In some implementations the method includes selecting laser parameters and method features to achieve a ratio of a cell size to a bubble size of one of: larger than 10, larger than 100, and larger than 1000.

In some implementations a laser system for fragmenting biological tissue includes a pulsed laser to produce a laser beam of pulses, and a laser control module to direct the laser beam to a selected target region of the tissue and to direct the laser beam to generate cell boundaries to form cells in the target region of the tissue.

In some implementations the laser control module is configured to form cells in a regular array.

In some implementations the laser control module formed to generate the laser pulses with laser parameters of at least one of: a pulse duration between 0.01 and 50 picoseconds, a repetition rate between 10 kHz and 100 megahertz, a pulse energy between 1 microJoule and 25 microJoule, and a pulse target separation between 0.1 micron and 50 microns.

In some implementations a method of fragmenting a tissue in an eye with a photodisruptive laser includes selecting a target region in the eye for fragmentation, and forming an array of cells in the target region by directing a beam of laser pulses to generate cell boundaries in the target region, with a cell size and laser parameters of the laser beam such that the tissue fragmentation requires a surgical time of less than two minutes, whereas a volumetric tissue fragmentation of the same target region with the same laser parameters would require a surgical time in excess of two minutes.

In some implementations the laser parameters are at least one of a pulse duration between 0.01 and 50 picoseconds, a repetition rate between 10 kHz and 100 MHz, a pulse energy between 1 microJoule and 25 microJoule, and a pulse target separation between 0.1 micron and 50 microns, and the cell size is between 1 microns and 50 microns.

DETAILED DESCRIPTION

Figure 1A:
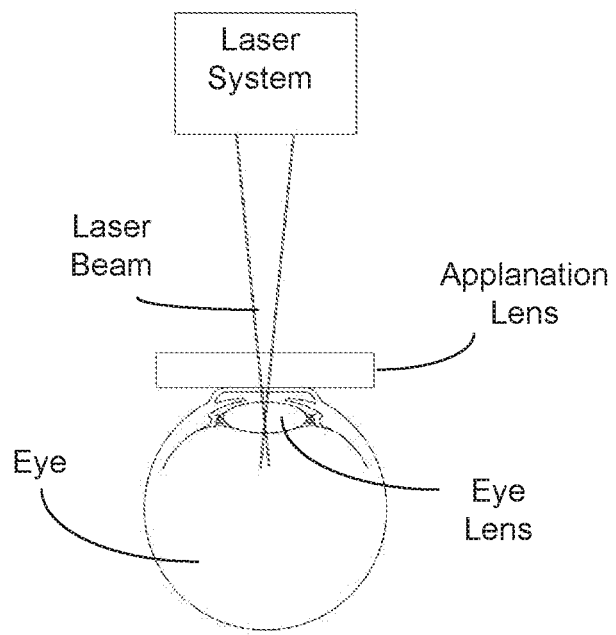
FIGS. 1a-c illustrate a volumetric eye disruption procedure.

This application describes examples and implementations of techniques and systems for laser surgery on the crystalline lens via photodisruption caused by laser pulses. Various lens surgical procedures for removal of the crystalline lens utilize various techniques to break up the lens into small fragments that can be removed from the eye through small incisions. These procedures may use manual mechanical instruments, ultrasound, heated fluids or lasers and tend to have significant drawbacks, including the need to enter the eye with probes in order to accomplish the fragmentation, and the limited precision associated with such lens fragmentation techniques. Photodisruptive laser technology can deliver laser pulses into the lens to optically fragment the lens without the insertion of a probe and thus can offer the potential for lens removal with improved control and efficiency. Laser-induced photodisruption has been widely used in laser ophthalmic surgery. In particular, Nd: YAG lasers have been frequently used as the laser sources, including lens fragmentation via laser induced photodisruption.

In a laser-induced lens fragmentation process, laser pulses interact with the lens tissue to generate gas in form of cavitation bubbles and decrease the lens tissue transparency. Because the laser pulses are sequentially delivered into the lens, the cavitation bubbles and reduced lens tissue transparency caused by the initial laser pulses can obscure the optical path of subsequent laser pulses and thus can interfere with the delivery of subsequent laser pulses directed to additional target positions in the lens by blocking, attenuating or scattering the subsequent laser pulses. This effect can reduce the actual optical power level of the subsequent laser pulses and thus adversely affect fragmentation at the deeper locations in the lens. Some known laser-induced lens fragmentation processes do not provide effective solutions to address this technical issue.

Based on effects of distinct regional properties of the lens and laser pulse parameters on spreading of gas produced during photodisruption, techniques, apparatus and systems described in this application can be used to effectively fragment the crystalline lens to remove a portion of or the entirety of the lens by using photodisruptive laser pulses with reduced interference caused by laser-induced air bubbles in the eye during the photodisruption process. The present methods and apparatus allow fragmentation of the entire or significant portions of the crystalline lens utilizing a photodisruptive laser delivered with minimized interference from gas generated during photodisruption. In addition to reduced gas generation the method allows the use of significantly less total laser energy to treat the eye and reduces potential undesired effects such as heat generated by the laser and reduces overall procedure time. The removal of a portion of or the entirety of the crystalline lens can be achieved via aspiration with reduced or no need of other lens fragmentation or modification modalities.

The crystalline lens has multiple optical functions in the eye, including preservation of a transparent optical path and dynamic focusing capability. The lens is a unique tissue in the human body in that it continues to grow in size during gestation, after birth and throughout life. Since new lens fiber cells are added from a germinal center located on the equatorial periphery of the lens, the oldest lens fibers are located centrally in the lens. This region, called the lens nucleus, has been further subdivided into embryonal, fetal and adult nuclear zones. While the lens increases in diameter, it may also undergo compaction so that the properties of the nucleus are different from the cortex (Freel et al BMC Ophthalmology 2003, 3:1). In addition, since lens fiber cells undergo progressive loss of cytoplasmic elements and since there is no blood supply or lymphatics to supply the inner zone of the lens, it becomes progressively more difficult to preserve the optical clarity and other properties (e.g., lens flexibility) that serve the function of the lens. Of particular importance is the central core of the lens, occupying the inner approximately 6-8 mm in equatorial diameter and approximately 2-3.5 mm in axial diameter. This region has been shown to have reduced permeability to and from the metabolically active cortex and outer nucleus (Sweeney et al Exp Eye res, 1998: 67, 587-95). A correlation with this observation is the progressive loss of transparency that is identified in the most common type of cataract in the same region in patients, as well as increases in lens stiffness that occur with age in a gradient fashion from the peripheral to central portion of the lens (Heys et al Molecular Vision 2004: 10:956-63). One result of such changes is the development of presbyopia and cataract that increase in severity and incidence with age.

The above identification of a central zone with different transport, optical and biomechanical properties has significant implications for fragmentation techniques with photodisruption, because one significant limitation to various laser-based lens fragmentation techniques is the uncontrolled spread of gas bubbles that can occur during photodisruption that can reduce the effectiveness of subsequent laser pulses in interacting with the lens. The layered structure of the lens body at different locations exhibits differing resistance to spread of cavitation bubble gas. Additionally, the softer peripheral layers can be sufficiently soft so as not to require photodisruption and/or significant fragmentation prior to aspiration and removal. These softer, less resistant peripheral layers however can allow the gas generated by photodisruption to spread and block subsequent laser pulses that are directed to fragment the harder central core. The precise determination of regions of a lens that are more or less resistant to the spread of cavitation bubble gas depends on individual characteristics of each patient including the age of the patient. The spread of gas can also be influenced by the particular laser parameters and treatment pattern applied to the target.

Figure 1B:
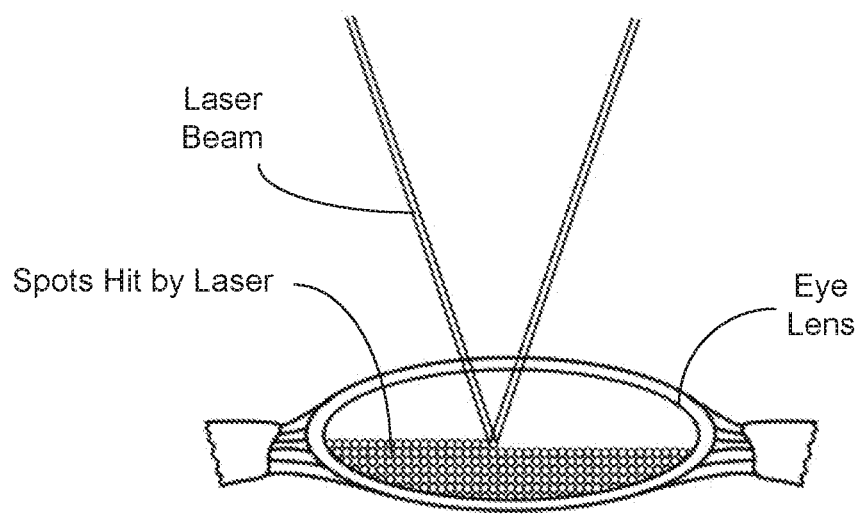
Figure 1C:
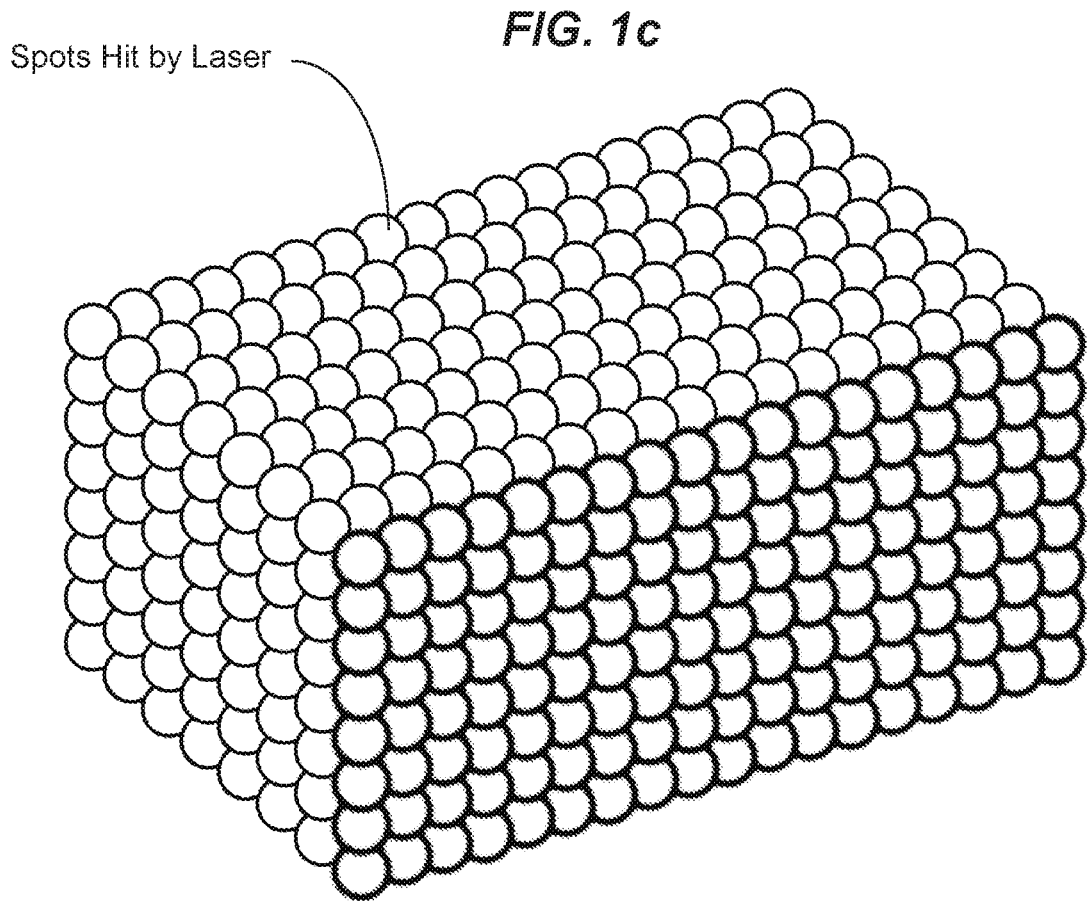

The tissue of the lens can be treated in an essentially uniform fashion. FIGS. 1a-c illustrate an example where a photodistruptive laser system is operated to place laser pulses essentially uniformly within a surgical region, e.g., the eye lens, to be treated to allow aspiration and removal of the lens material. One way to fill the volume with laser is to direct the laser pulses with a scanner to form a bubble layer and fill the entire volume with a multitude of layers, as shown in FIG. 1c.

Figure 2:
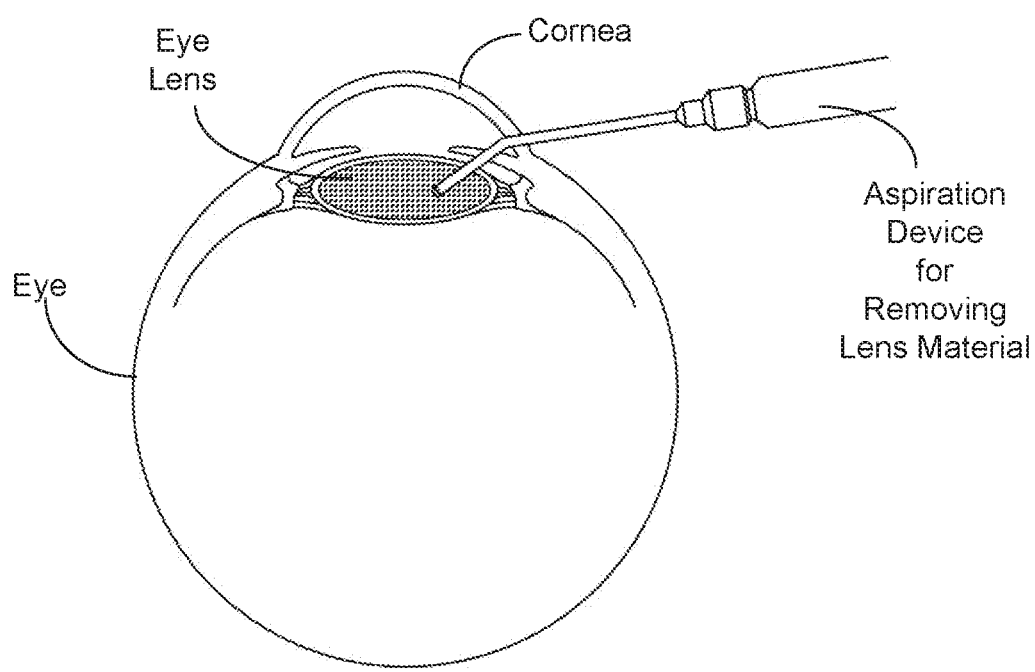
FIG. 2 illustrates an aspiration step.

FIG. 2 illustrates that after the laser treatment, an aspiration device can be used to remove the disrupted lens material.

In such procedures, the laser pulse characteristics, such as their duration can range from 0.01 picoseconds (ps) to 50 picoseconds. The laser pulse energy, layer, line and spot separations can be optimized to achieve the highest effectiveness of breaking up the tissue wile minimizing the effects of gas spreading, laser exposure and procedure time.

One determining factor of the laser pulse characteristics is the need to avoid or minimize a triggering of an uncontrolled gas spreading. Since the conditions and properties of the lenses can vary from patient to patient, the threshold laser pulse parameters to achieve this can vary as well. In some implementations, the laser energy per pulse can range from 1 microJoule (µJ) to 25 µJ and the spatial pulse separation between two initial pulses adjacent in space can fall within the range of 0.1 micron to 50 microns. The laser pulse duration can range from 0.01 picoseconds to 50 picoseconds and the laser repetition rate from 10 kHz to 100 MHz.

The parameters of the laser pulses and the scan pattern can be determined by various methods. For example, they can be based on a preoperative measurement of the lens optical or structural properties. The laser energy and the spot separation can also be selected based on a preoperative measurement of lens optical or structural properties and the use of an age-dependant algorithm. The pulsed laser is operated to direct a sequence of laser pulses to a target lens region of the lens to fragment the target lens region. The laser pulses may also be directed to one or more regions of the lens other than the target lens region, e.g., peripheral locations and/or the lens capsule, to create an opening or incision in the lens. After the desired fragmentation and incision are achieved, the laser pulses can be terminated and the fragmented target lens region and any other selected portions of the lens are removed from the lens body by aspiration.

The following sections describe techniques and laser systems for applying laser pulses to surfaces and boundaries of cells of predetermined size, shape and spatial distribution that differ from the above described uniform volumetric distribution of the laser pulses within the treated volume. Following such a laser treatment the lens tissue can subsequently break up along the surfaces and boundaries of the cells. The size of the cells or granules can be determined to be small enough that they can easily be removed by using e.g. an aspiration device. A typical aspiration device is a needle attached to a suction pump. For example a 23 gauge needle has an inner diameter of 0.34 mm. Cells smaller than the inner diameter of the aspiration needle can pass through the needle without clogging.

Figure 3:
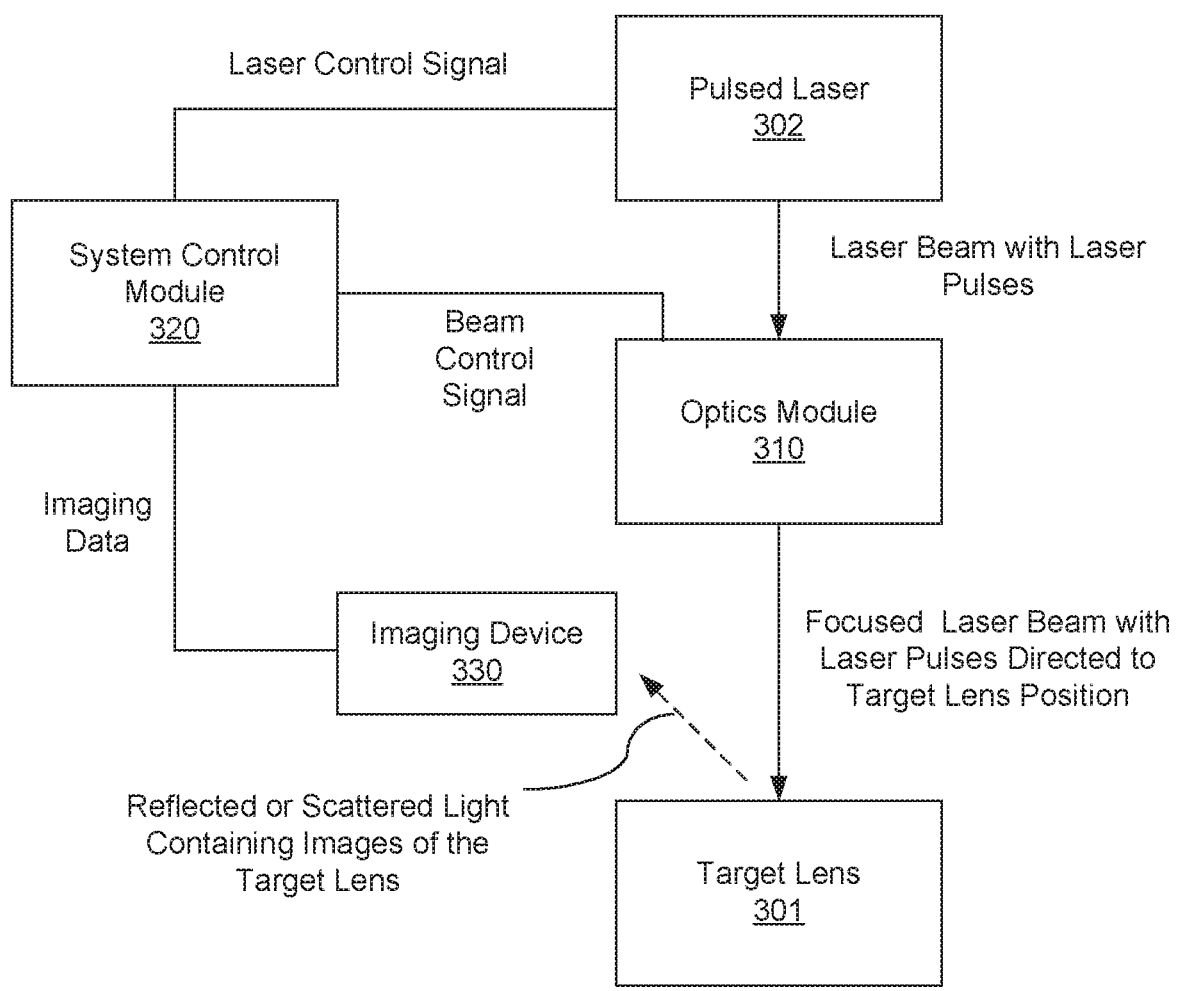
FIG. 3 illustrates an ophthalmic surgery system.

FIG. 3 illustrates a laser surgical system for performing such a non-uniform laser distribution process. An optics module 310 can focus and direct the laser beam to a target lens 301. The optics module 310 can include one or more lenses and may further include one or more reflectors. A control actuator can be included in the optics module 310 to adjust the focusing and the beam direction in response to a beam control signal. A system control module 320 can control both a pulsed laser 302 via a laser control signal and the optics module 310 via the beam control signal. An imaging device 330 may collect reflected or scattered light or sound from the target lens 301 to capture image data via the target lens 301. The captured image data can then be processed by the laser system control module 320 to determine the placement of the applied laser pulses. This control can be a dynamic alignment process during the surgical process to ensure that the laser beam is properly directed at each target position. The imaging device 330 can be implemented in various forms, including an optical coherent tomography (OCT) device. In other implementations, an ultrasound imaging device can also be used.

The system control module 320 may process image data from the imaging device 330 that includes the position offset information for the photodisruption byproducts in the target region. Based on the offset information obtained from the image data, the beam control signal can be generated to control the optics module 310, which can adjust the laser beam in response. A digital processing unit can be included in the system control module 320 to perform various data processing functions for the laser alignment and laser surgery. The digital processing unit can be programmed to control the laser parameters of the initial laser pulses and the additional laser pulses, laser beam scanning direction from the posterior to anterior direction for the initial laser pulses and the laser movement of the additional laser pulses.

In one implementation, the pulsed laser 302 can be a high repetition rate pulsed laser at a pulse repetition rate of thousands of shots per second or higher with relatively low energy per pulse. Such a laser can be operated to use relatively low energy per pulse to localize the tissue effect caused by laser-induced photodisruption. A form of this tissue effect is the formation of cavitation bubbles. In some implementations, the impacted tissue region can have a size of the order of microns or tens of microns. This localized tissue effect can improve the precision of the laser surgery and can be desirable in certain ophthalmic surgical procedures. In one example of such surgery, placement of many hundred, thousands or millions of contiguous or near contiguous pulses, which may be separated by microns or tens of microns, can be used to achieve certain desired surgical effect placement. Such procedures using high repetition rate pulsed lasers may require high precision in positioning each pulse in the target region during surgery, both regarding their absolute position with respect to a target location and their relative position with respect to preceding pulses. For example, in some cases, subsequent laser pulses may be required to be delivered next to each other with an accuracy of a few microns, when the time between pulses (the repetition rate) can be of the order of microseconds.

Figure 4A:
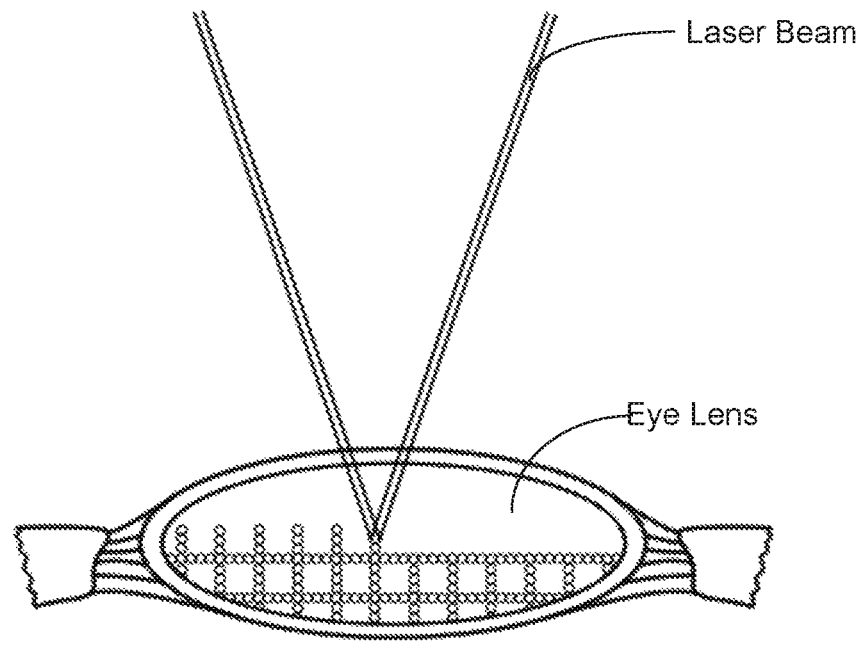
FIGS. 4a-b illustrate a regular cell array.
Figure 4B:
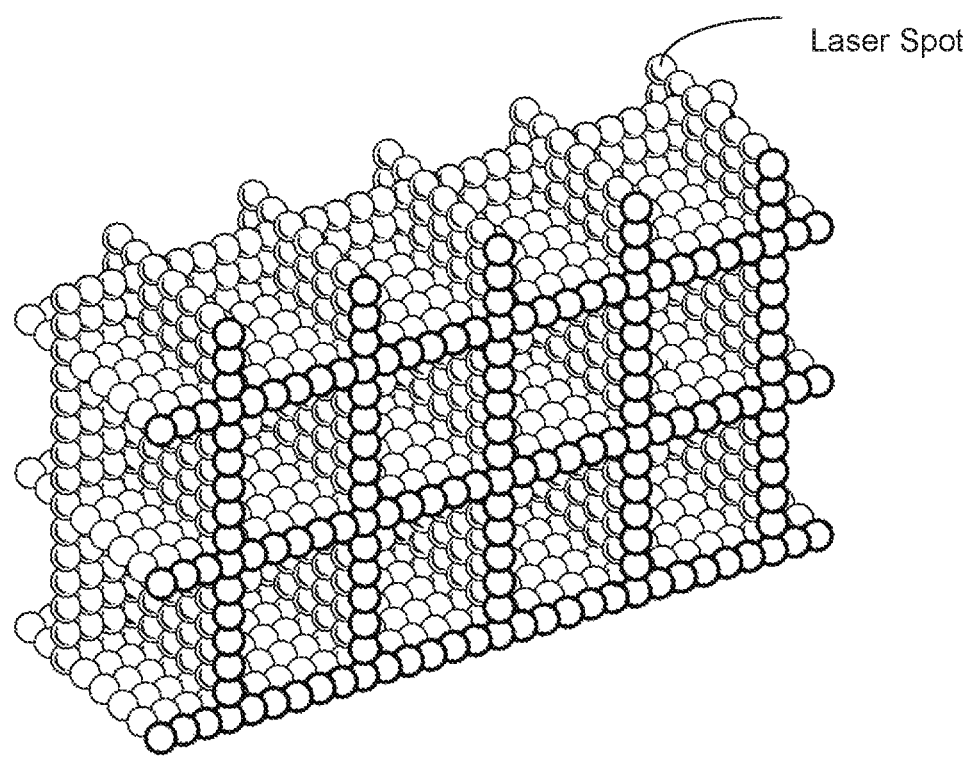

FIGS. 4a-b show an implementation of an ophthalmic surgical procedure, during which laser spots (or bubbles) are generated to form granules, the granules themselves forming a granule array. The laser spots can be generated to form a regular spatial pattern of the granules, as shown in FIG. 4b. Regularly spaced granules utilize the laser pulses well, since they require a limited amount of laser energy to break up a target region. Nevertheless, in other implementations the granules may form an irregular or even random array.

The cells can be packed next to one another. Creating the side wall of one cell can simultaneously create the side of the neighboring cell as well, making the process efficient. The design of the individual cells and the cell pattern may be selected based on the physical properties of the tissue to be treated. The bulk of the lens consists of concentric layers of elongated fiber cells. Cleavage of tissue parallel and perpendicular to the layers and individual fibers is different. Therefore, in some implementations a higher spot density and/or laser pulse energy can be used to form cell boundaries which are perpendicular to layers and fibers.

During the formation of a particular spatial pattern, different implementations of the present surgical method may utilize different scanning paths. A regular pattern can be built all at once or granule by granule. Which method to use may depend on the particular laser scanner and it is a matter of optimization to achieve higher precision and shorter procedure time.

In a particular implementation the granules, or cells, can be cubes. With an analogy to crystal cell structures, this pattern of cells can be described as a Simple Cubic (SC) crystal. Layers of these cubes can be formed simultaneously, followed by repeating the procedure in subsequent layers.

Figure 4C:
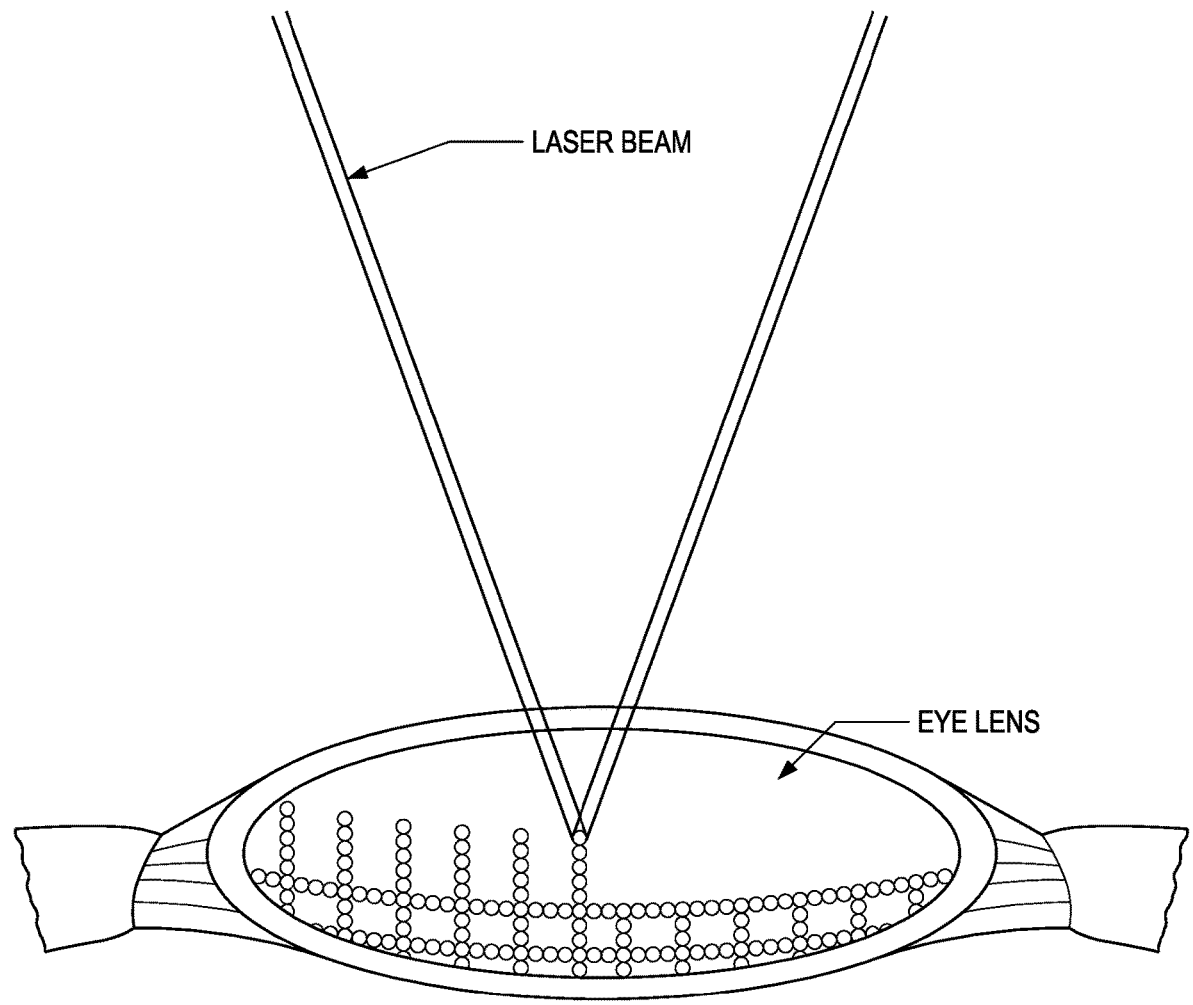
FIG. 4c illustrates a cell array with layers that are curved.

FIG. 4c illustrates a cell array with layers that are curved. The layers can be somewhat curved, to accommodate the natural curvature of the lens target region itself or the natural curvature of the focal plane of the surgical system. The layers are created by causing the optics to scan the pulsed laser according to a curvature of a focal plane of the optics to track a natural curvature of the lens.

Figure 5A:
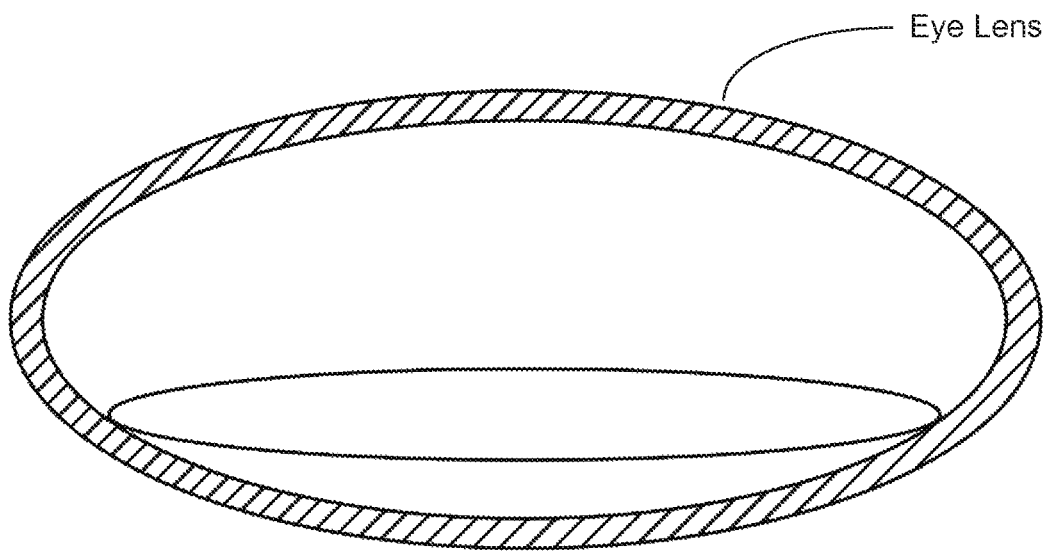
FIGS. 5a-d illustrate a layer-by-layer formation of a cell array.

FIGS. 5a-d illustrate that in some implementations first a bubble layer can be generated with the laser pulses to form the bottom layer of the SC crystal, as shown in FIG. 5a. In some implementations, this bottom layer can be essentially transverse, or perpendicular, to an optical axis of the lens or the eye. As it is known, an optical axis can be defined in several different ways, with somewhat different outcomes. In what follows, the term "optical axis" will be used to refer to an axis defined by any one of these procedures, or even a compromise axis, defined as a direction falling between differently defined axes.

Figure 5B:
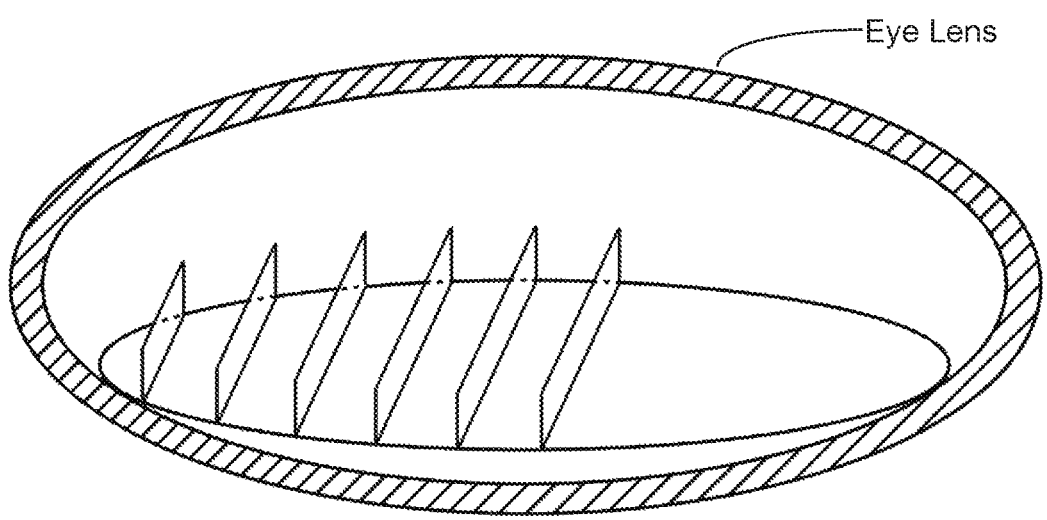

FIG. 5b illustrates that subsequent to the formation of the bottom layer, a regular array of cell walls can be generated. These walls can be essentially parallel to the optical axis, formed with a predetermined cell height.

Figure 5C:
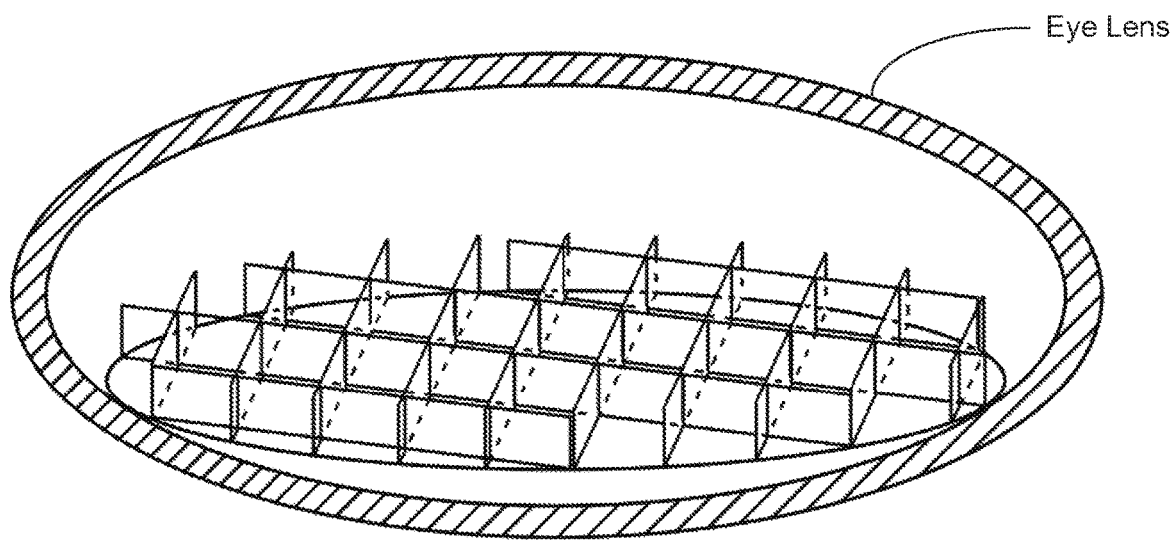

FIGS. 5b and 5c illustrate that the scanner can raster, or sweep, first in one direction (FIG. 5b) then in an orthogonal direction (FIG. 5c).

Figure 5D:
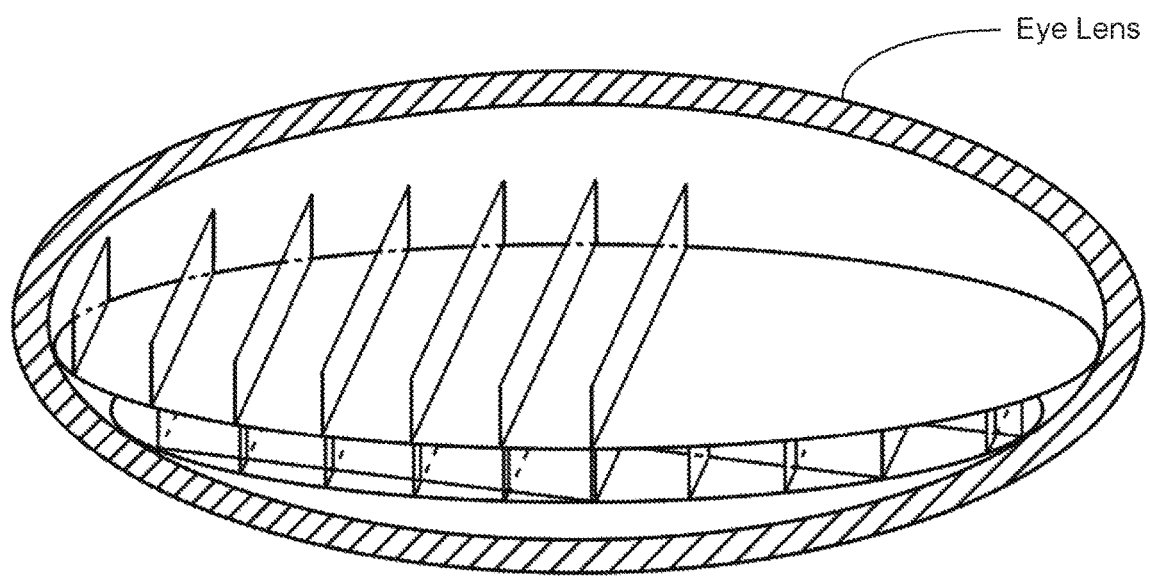

FIG. 5d illustrates that a layer of cells can be completed by placing a bubble-layer to form the top of the cells. This "top" bubble-layer can then form the bottom bubble-layer for the next layer of cells. The target volume can be filled up with a regular array of granules/cell by repeating the steps 5a-d.

In some implementations, a smooth boundary layer can be formed around the regular array of cells in the surgical target region, partially, or in its entirety. Such a boundary layer can provide a smooth surface without the raggedness of the edges of the cell array.

In other implementations, the crystalline cell array/structure can be oriented differently, the bottom layer forming any angle with the optical axis of the eye. In yet other implementations, the layers themselves can be somewhat curved, to accommodate the natural curvature of the lens target region itself or the natural curvature of the focal plane of the surgical system. Such structures may not be entirely regular. They may contain deformations or lattice defects. These defects can be formed intentionally or may emerge during the creation of the cell array.

Figure 6A:
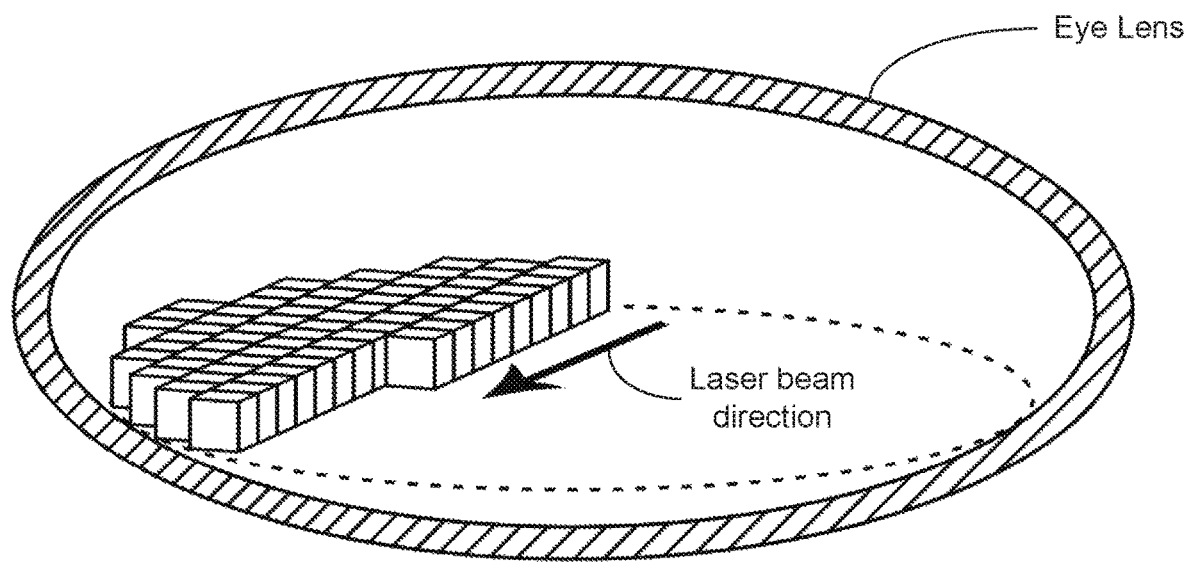
FIGS. 6a-b illustrate a formation of a cell array on a cell-by-cell basis.
Figure 6B:
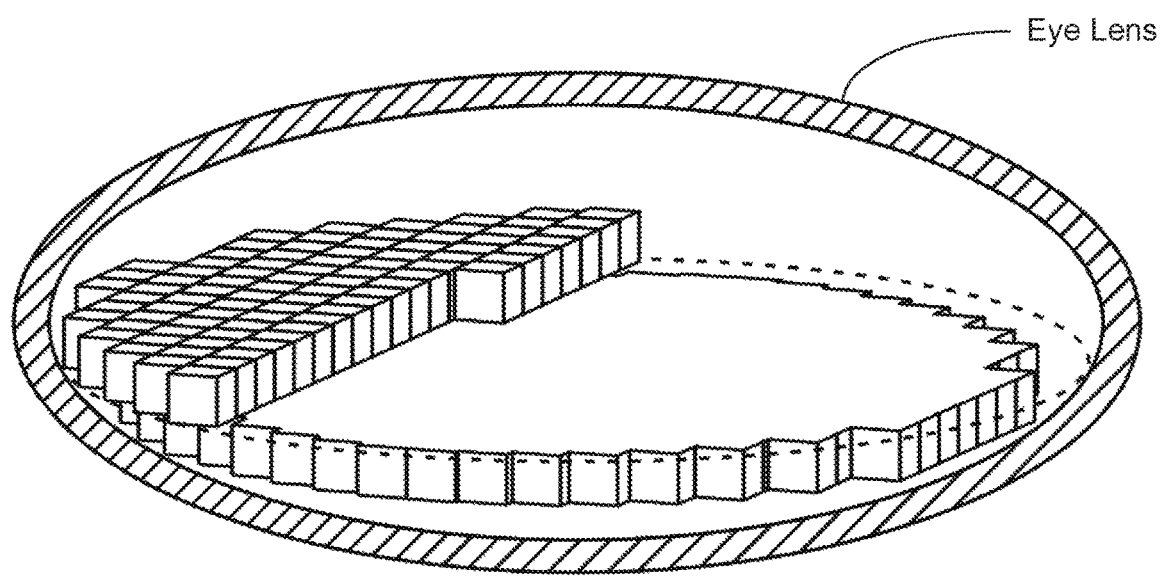

FIGS. 6a-b illustrate an alternative implementation, where complete cells of a layer can be formed individually one after the other by controlling the scanner to form all walls of a single cell, and to start forming the next cell only after the previous cell is completed.

FIG. 6a illustrates that rows of cells can be formed first to build a layer of cells.

FIG. 6b illustrates that subsequent layers can be formed on top of already created layers, to fill a surgical target volume.

The implementations which form the cells individually may have the following features.

Figure 7A:
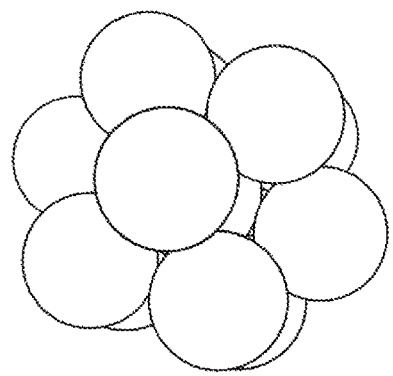
FIGS. 7a-c illustrate spherical and polyhedral cell structures.
Figure 7B:
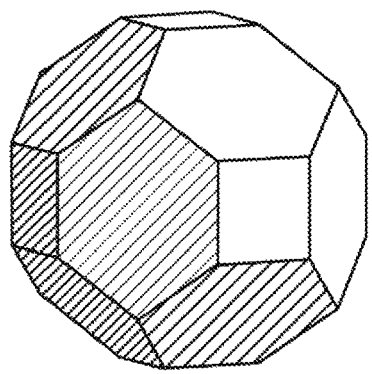
Figure 7C:
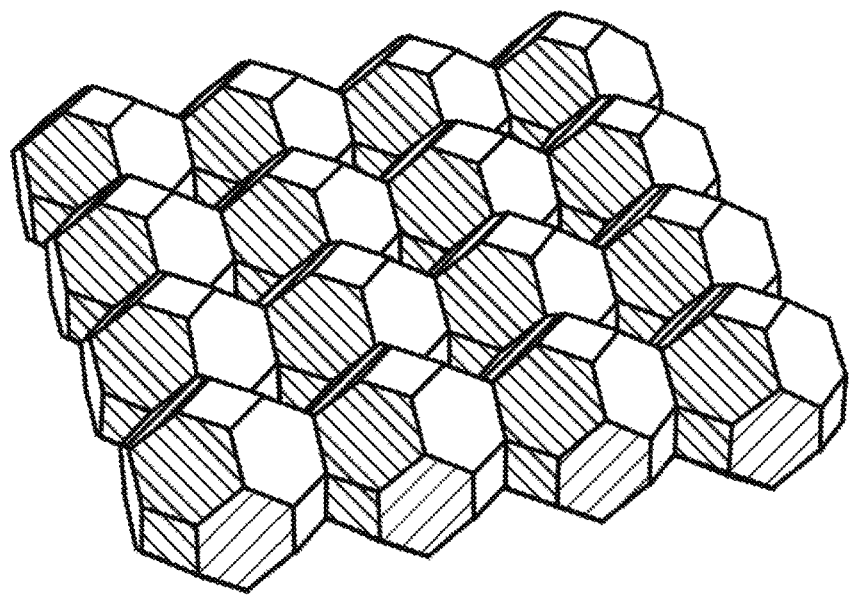

First, FIGS. 7a-c illustrate that the shape of the cells can be different from the simplest shapes, like cubes. For example, the cell array can have a hexagonal base to form a Simple Hexagonal (SH) lattice. Or a target volume can be broken up into cells of a different type, such as spheres (FIG. 7a), separated by complementary small interstitial regions. Spherical cell shapes can minimize the occurrence of clogging in the aspiration needle. The type of the lattice, formed by the spherical cells can be selected to optimize the ratio of the volume of the spheres to the volume of the interstitial regions. These lattice types are known as "close packed" crystals structures. Face Centered Cubic (FCC) and Hexagonal Closest Packing (HCP) are two such structures.

In some implementations, the cells can have shapes which approximate spheres, such as polyhedral shapes. In these implementations, the polyhedral cells can form close packed structures, analogously to the lattice of spheres.

FIG. 7b illustrates a Truncated Rhombic Dodecahedron, which is an example of a polyhedron approximating a sphere.

FIG. 7c illustrates that truncated rhombic dodecahedrons can be close packed to form a layer, and fill a target volume with a stack of layers. When passing through the aspiration needle, these polyhedra can more readily roll than cubes and the likelihood of clogging is smaller.

Second, the laser scanner pattern can be optimized to speed up completion of the whole pattern. Creating individual cells with sizes of the order of 100 to 200 micrometers require small scanner displacements and can be performed at higher scanner speed. Larger scale moves of the scanner can be slower. The design of the scanner can be optimized effectively for achieving the shortest overall procedure time. Applying a combination of two different scanner types, a fast small displacement scanner and a slow but larger displacement scanner, can further optimize system performance. Building cells individually is also consistent with modular software design practices. A complete volumetric pattern can be created from building blocks; cells, rows and layers of cells and finally the complete pattern. An analogous approach can be effective in constructing a software code for the scanner drivers as well.

The above described or other patterns can be created by proceeding from the posterior to the anterior side of the lens or from the anterior to the posterior side. The former can be advantageous to avoid blocking the laser beam by bubbles previously formed in the target tissue. The latter may be preferable when a cataract is present in the lens and penetration of laser light through the cataract is already compromised. In that case fragmentation of the anterior portion of the lens may be necessary followed by aspiration of the treated portion and successive laser treatment and aspiration of the deeper-lying parts of the lens until the full volume is fragmented.

Additional features of implementations which fragment the target tissue in a granular or cellular form include the following.

1) Reduction of the amount of gas bubbles formed in the eye and thus reduction of the induced opacity of the tissue. Since a similar degree of tissue disruption can be achieved by considerably smaller number of bubbles in a granular/cellular procedure, this aspect can increase the effectiveness of the laser treatment to a substantial degree.

2) Reduction of the number of pulses applied to the tissue, which increases the speed of the procedure. Time is at a premium during eye surgery, as after about two minutes patients sometimes develop an increasing, hard-to-control eye movement. This can necessitate the abandonment of the surgical procedure. Therefore, if a new feature in a surgical procedure is capable of reducing a time of the surgery from above two minutes to below two minutes, that feature may increase the utility of the surgical procedure qualitatively.

3) Reduction of the required total energy applied to the tissue, which reduces potential undesired side-effects related to the exposure of the eye to laser light. In most procedures, a substantial portion of the laser light passes through the surgical region and continues its way to the retina. The retina being a strongly light sensitive tissue itself, this transmitted surgical laser light may damage the retina to an undesirable or unacceptable degree. Thus, a reduction of the transmitted laser light can be an advantageous feature.

To quantitatively assess the different implementations, a comparison is provided for the amount of laser energy required for treating a given volume, and for the number of laser pulses required for volumetric and cellular fragmentation procedures.

TABLE 1

| Spot separation (um) | Cube size (um) | Number of pulses per mm³ volumetric breakdown | Number of pulses per mm³ granular breakdown | Ratio of pulses, volumetric vs. granular, ratio of procedure time |
|---|---|---|---|---|
| 2 | 50 | 125000000 | 14400000 | 8.7 |
| 2 | 150 | 125000000 | 4933333 | 25.3 |
| 2 | 250 | 125000000 | 2976000 | 42.0 |
| 5 | 50 | 8000000 | 2160000 | 3.7 |
| 5 | 150 | 8000000 | 773333 | 10.3 |
| 5 | 250 | 8000000 | 470400 | 17.0 |
| 10 | 50 | 1000000 | 480000 | 2.1 |
| 10 | 150 | 1000000 | 186667 | 5.4 |
| 10 | 250 | 1000000 | 115200 | 8.7 |
| 20 | 50 | 125000 | 90000 | 1.4 |
| 20 | 150 | 125000 | 43333 | 2.9 |
| 20 | 250 | 125000 | 27600 | 4.5 |

Table 1 illustrates some results of the comparison, contrasting tissue breakdown by performing a volumetric method and by forming a Simple Cubic lattice of cells. Typically, the volume of an individual gas bubbles is approximately proportional to the energy of the femtosecond laser pulse which created the bubble. This proportionality holds for energies not too close to the threshold of producing plasma. Further, the individual pulses are directed such that the gas bubbles touch each other. In the volumetric method this translates to the spot, line, and layer separation being approximately equal to one another, all being set by the diameter of the bubbles. In the cellular implementation this translates to the cell boundaries being formed by touching spheres. It is noted that in practice, some overlap may be necessary for both volumetric and cell-array methods.

Table 1 reports comparison results, varying the spot separation from 2 microns to 20 microns and the cell size from 50 microns to 300 microns. The speed of the procedure was characterized by the number of pulses needed for a given total volume and the total energy needed.

In some implementations of the volumetric breakdown, the total energy needed to break down the tissue in the target region can be approximately independent of the size of the bubbles. This energy is of the order of 1 Joule per cubic millimeter of target volume. This relationship holds most accurately in the energy range in which the volume of an individual bubble is proportional to the laser pulse energy.

For implementations which form a lattice of cells, the speed and the corresponding energy depends both on the size of the individual bubbles and on the size of the cell. The speed increases with increasing cell sizes and decreasing bubble sizes. This is the result of the change in the volume to surface ratio of the cells as a function of their size. This comparison is based on using a 23 gauge needle which has inner diameter of 340 micrometers. The largest size cube which can enter the tube at the least favored orientation, with its body diagonal perpendicular to the length of the tube, is about 196 micrometers. Actual implementations may use smaller grain sizes, such as 150 microns.

As Table 1 illustrates, methods based on forming cell-lattices can exhibit an increase of speed by a factor of 2.9 to 25.3 over the speed of the volumetric method as the size of the bubbles is varied. For a typical bubble size of 10 microns, the increase of speed can be about 5.4-fold. The speed ratio increases with decreasing bubble size. The improvement in the procedure time is approximately a factor of 10 for 5 micron bubble size and 25 for 2 micron bubble sizes. These are quite significant improvements over the volumetric method.

As mentioned above, the required total laser energy is proportional to the total volume of gas produced, which is proportional to the number of bubbles for bubbles of a fixed size. Therefore, among methods which use the same average laser power and create similarly sized bubbles, the procedure time is approximately proportional to the number of bubbles created. Thus, the speed improvement of the cell-array methods over the volumetric methods is proportional to the ratio R of the total number of pulses, as demonstrated in Table 1. Implementations with a different bubble size in general require different laser average power, repetition rate, and scanner speed setting. Nevertheless, it remains true for implementations with all bubble sizes that granular/cellular fragmentation decreases the total energy and time required compared to volumetric fragmentation with the same bubble size. Thus $$R = \frac{\text{Volume\_of\_gas\_produced\_in\_volumetric\_fragmentation}}{\text{Volume\_of\_gas\_produced\_in\_granular\_fragmentation}} \quad (1)$$

Also, $$R = \frac{\text{Procedure\_time\_of\_volumetric\_fragmentation}}{\text{Procedure\_time\_of\_granular\_fragmentation}} \quad (2)$$

When the cell size is significantly larger than the bubble size, R can be approximately proportional to the Volume/Surface ratio of the cell. Since the volume of gas produced is approximately proportional to the product of the area of the cell boundaries multiplied with the bubble size, R is approximately proportional to a ratio of a cell size to a bubble size.

$$R \propto \frac{\text{Cell\_size}}{\text{Bubble\_size}}. \quad (3)$$

Granular fragmentation with the smallest bubble size produces the smallest amount of gas in the target tissue and uses the smallest amount of total laser energy. In some implementations there can be a practical limit, how small a bubble size should be used. In some implementations the bubbles are closely packed, and the corresponding spot separation and line separation is nearly equal to the bubble size when creating the surface of a cell boundary. Although the laser parameters, average power, pulse energy and repetition rate can be chosen over a wide enough range to achieve the desired bubble size, spot and line separations, the scanning system can be limited in its speed and acceleration to generate a particular pattern. To keep the acceleration of the scanner under control at turning points, in some implementations the linear speed of progression of the bubble placement can be kept smaller than a limiting value, $v_{lim}$.

For a given granular pattern the total area of the cell boundaries, A, and as demonstrated in Table 1. the total number of pulses N per total volume are given for given bubble size. For example, for a close packed area $A=N*bubble\_size^2$.

The total linear path of bubble placement s may equal $N*bubble\_size$, which is also the speed of progression of bubble placement times the total procedure time, $s=v*T$. Therefore, in some approaches, the product $v*T*bubble\_size$ may be approximately constant.

In order to minimize the total amount of gas produced and the total amount of laser energy used for a granular pattern, some approaches minimize the bubble size by selecting the linear speed of progression and the procedure time to their largest acceptable value $v_{lim}$ and $T_{max}$. Here $T_{max}$ is the maximum procedure time tolerable by the clinical environment, less than 1 minute is acceptable, less than 30 seconds is desirable, dictated mainly by the tolerance of the patient to keep still during the procedure.

On the other hand, to minimize procedure time, the highest linear speed $v_{lim}$ and the largest acceptable bubble size can be selected. The largest acceptable bubble size is determined by the amount of gas produced, pulse energy used, and by the required precision of the surgery.

Some implementations of the surgical system maximize the speed of scanner and lower the laser energy threshold for the formation of cavitation bubbles, in order to minimize bubble size. The surgeon has the choice to select particular parameters within the limitation of the surgical system to optimize the parameters for particular surgical outcomes. The decision may take into account the size of the surgically affected area, tissue parameters the age of the patient and other factors.

While this specification contains many specifics, these should not be construed as limitations on the scope of an invention or of what may be claimed, but, rather, as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. An ophthalmic laser surgical system, comprising:
a pulsed laser source configured to generate a pulsed laser beam;
an imaging device configured to capture image data and measure structural properties of a lens of an eye;
an optics module with optics configured to direct the laser beam towards a plurality of target regions in the lens of the eye, wherein the laser beam is applied as a plurality of spots at the target regions, wherein the plurality of spots are generated in a laser pattern with a spot separation selected based on the structural properties of the lens, wherein at least a portion of the target regions include a bulk portion of the lens having concentric layers of elongated fibers; and
a system control module configured to control, based on the image data and the structural properties of the lens, the optics module to form an array of cells in the target region by creating a plurality of layers of photodisrupted bubbles and a plurality of walls of photodisrupted bubbles to generate cell boundaries, wherein the system control module is further configured to control the optics module to direct pulsed laser source to generate the laser pattern with a spot separation with a higher spot density and/ or a higher laser pulse energy to form cell boundaries that are perpendicular to the elongated fibers, as compared to when the cell boundaries are located parallel to elongated fibers.

2. The system of claim 1, wherein the array of cells are of a size suitable for extraction by aspiration without manual lens fragmentation.

3. The system of claim 1, wherein a spatial extent of the array of cells is less than 340 microns.

4. The system of claim 1, wherein the array of cells comprises cells greater than 50 microns.

5. The system of claim 1, wherein the array of cells includes a set of cells in a periodically repeating array.

6. The system of claim 1, wherein the array of cells comprises cells greater than 250 microns.

7. The system of claim 1, wherein the system control module is configured to control the optics to form the bubbles with a spot separation of less than 20 microns.

8. The system of claim 1, wherein the system control module is configured to control the optics module to reduce a linear speed of progression of a bubble placement at turning points to a speed that is smaller than a limiting value, a turning point being a point where there is a change in direction.

* * * * *